(12) United States Patent
Hirose et al.

(10) Patent No.: US 8,173,859 B2
(45) Date of Patent: May 8, 2012

(54) EPILEPSY MODEL ANIMAL

(75) Inventors: Shinichi Hirose, Fukuoka (JP); Sunao Kaneko, Aomori (JP); Motohiro Okada, Aomori (JP); Ryo Saito, Fukuoka (JP)

(73) Assignee: Japan Science and Technology Agency, Saitama (JP)

( * ) Notice: Subject to any disclaimer, the term of this patent is extended or adjusted under 35 U.S.C. 154(b) by 828 days.

(21) Appl. No.: 10/591,587

(22) PCT Filed: Feb. 23, 2005

(86) PCT No.: PCT/JP2005/003430
§ 371 (c)(1),
(2), (4) Date: Oct. 23, 2006

(87) PCT Pub. No.: WO2005/084428
PCT Pub. Date: Sep. 15, 2005

(65) Prior Publication Data
US 2008/0148417 A1    Jun. 19, 2008

(30) Foreign Application Priority Data
Mar. 5, 2004    (JP) .................. 2004-062907

(51) Int. Cl.
*A01K 67/00*     (2006.01)
*A01K 67/027*    (2006.01)
*G01N 33/00*     (2006.01)
*C12N 15/00*     (2006.01)
*C07H 21/04*     (2006.01)

(52) U.S. Cl. ......... 800/9; 800/3; 800/8; 800/13; 800/14; 800/25; 435/455; 536/23.1; 536/23.5; 536/24.1

(58) Field of Classification Search ................. None
See application file for complete search history.

(56) References Cited

OTHER PUBLICATIONS

Rulicke and Hubischer, 2000, Experimental Physiology 85: 589-601.*
McColl et al 2003, Neuropharmacology 44:234-243.*
Saito et al., "Characteristics of transgenic rats harboring a mutation underlying human autosomal dominant nocturnal frontal lobe epilepsy (ADNFLE)", J. Pharmacol. Sci., vol. 23, No. 94, Suppl. I, p. 102, Feb. 2004.
Hirose et al., "A novel mutation of CHRNA4 responsible for autosomal dominant nocturnal frontal lobe epilepsy", Neurology, vol. 53, No. 8, pp. 1749-1753, Nov. 1999.
A. Rozycka et al., "Evidence for S284L mutation of the CHRNA4 in a white family with autosomal dominant nocturnal frontal lobe epilepsy", Epilepsia, vol. 44, No. 8, pp. 1113-1117, Aug. 2003.
N. Matsushima et al., "Mutation (Ser284Leu) of neuronal nicotinic acetylcholine receptor α4 subunit associated with frontal lobe epilepsy causes faster desensitization of the rat receptor expressed in oocytes", Epilepsy Research, vol. 48, pp. 181-186, 2002.

(Continued)

*Primary Examiner* — Robert M Kelly
*Assistant Examiner* — Kelaginamane T Hiriyanna
(74) *Attorney, Agent, or Firm* — Wenderoth, Lind & Ponack, L.L.P.

(57) ABSTRACT

An epilepsy model animal (CHRNA4:S284L) developing spontaneous epileptic seizure during sleep, which is a non-human animal established by ontogenesis of a totipotent cell into which a polynucleotide encoding nonhuman mutant CHRNA4 is introduced and having said polynucleotide in its somatic chromosome, or a progeny of the nonhuman animal, wherein said nonhuman mutant CHRNA4 has the corresponding mutation of human mutant CHRNA4 in which the 284th Ser of SEQ ID NO: 1 is substituted by Leu. The epilepsy model animal has gene abnormality homologous to human chromosomal dominant nocturnal frontal lobe epilepsy and a symptom (epileptic seizure during sleep) the same as that of human autosomal dominant nocturnal frontal lobe epilepsy.

2 Claims, 1 Drawing Sheet

OTHER PUBLICATIONS

E. Tribollet et al., "Role of neuronal nicotinic receptors in the transmission of processing of information in neurons of the central nervous system", Pharmacology, Biochemistry and Behavior, vol. 70, pp. 457-466, 2001.

* cited by examiner

SEQUENCE LISTING

```
<160> NUMBER OF SEQ ID NOS: 5

<210> SEQ ID NO 1
<211> LENGTH: 627
<212> TYPE: PRT
<213> ORGANISM: Homo sapiens

<400> SEQUENCE: 1

Met Glu Leu Gly Gly Pro Gly Ala Pro Arg Leu Leu Pro Pro Leu Leu
1               5                   10                  15

Leu Leu Leu Gly Thr Gly Leu Leu Arg Ala Ser Ser His Val Glu Thr
            20                  25                  30

Arg Ala His Ala Glu Glu Arg Leu Leu Lys Lys Leu Phe Ser Gly Tyr
        35                  40                  45

Asn Lys Trp Ser Arg Pro Val Ala Asn Ile Ser Asp Val Val Leu Val
    50                  55                  60

Arg Phe Gly Leu Ser Ile Ala Gln Leu Ile Asp Val Asp Glu Lys Asn
65                  70                  75                  80

Gln Met Met Thr Thr Asn Val Trp Val Lys Gln Glu Trp His Asp Tyr
                85                  90                  95

Lys Leu Arg Trp Asp Pro Ala Asp Tyr Glu Asn Val Thr Ser Ile Arg
            100                 105                 110

Ile Pro Ser Glu Leu Ile Trp Arg Pro Asp Ile Val Leu Tyr Asn Asn
        115                 120                 125

Ala Asp Gly Asp Phe Ala Val Thr His Leu Thr Lys Ala His Leu Phe
    130                 135                 140

His Asp Gly Arg Val Gln Trp Thr Pro Pro Ala Ile Tyr Lys Ser Ser
145                 150                 155                 160

Cys Ser Ile Asp Val Thr Phe Phe Pro Phe Asp Gln Gln Asn Cys Thr
                165                 170                 175

Met Lys Phe Gly Ser Trp Thr Tyr Asp Lys Ala Lys Ile Asp Leu Val
            180                 185                 190

Asn Met His Ser Arg Val Asp Gln Leu Asp Phe Trp Glu Ser Gly Glu
        195                 200                 205
```

-continued

Trp Val Ile Val Asp Ala Val Gly Thr Tyr Asn Thr Arg Lys Tyr Glu
    210             215             220
Cys Cys Ala Glu Ile Tyr Pro Asp Ile Thr Tyr Ala Phe Val Ile Arg
225             230             235             240
Arg Leu Pro Leu Phe Tyr Thr Ile Asn Leu Ile Ile Pro Cys Leu Leu
                245             250             255
Ile Ser Cys Leu Thr Val Leu Val Phe Tyr Leu Pro Ser Glu Cys Gly
            260             265             270
Glu Lys Ile Thr Leu Cys Ile Ser Val Leu Leu Ser Leu Thr Val Phe
        275             280             285
Leu Leu Leu Ile Thr Glu Ile Ile Pro Ser Thr Ser Leu Val Ile Pro
    290             295             300
Leu Ile Gly Glu Tyr Leu Leu Phe Thr Met Ile Phe Val Thr Leu Ser
305             310             315             320
Ile Val Ile Thr Val Phe Val Leu Asn Val His His Arg Ser Pro Arg
                325             330             335
Thr His Thr Met Pro Thr Trp Val Arg Arg Val Phe Leu Asp Ile Val
            340             345             350
Pro Arg Leu Leu Leu Met Lys Arg Pro Ser Val Val Lys Asp Asn Cys
        355             360             365
Arg Arg Leu Ile Glu Ser Met His Lys Met Ala Ser Ala Pro Arg Phe
    370             375             380
Trp Pro Glu Pro Glu Gly Glu Pro Pro Ala Thr Ser Gly Thr Gln Ser
385             390             395             400
Leu His Pro Pro Ser Pro Ser Phe Cys Val Pro Leu Asp Val Pro Ala
                405             410             415
Glu Pro Gly Pro Ser Cys Lys Ser Pro Ser Asp Gln Leu Pro Pro Gln
            420             425             430
Gln Pro Leu Glu Ala Glu Lys Ala Ser Pro His Pro Ser Pro Gly Pro
        435             440             445
Cys Arg Pro Pro His Gly Thr Gln Ala Pro Gly Leu Ala Lys Ala Arg
    450             455             460
Ser Leu Ser Val Gln His Met Ser Ser Pro Gly Glu Ala Val Glu Gly
465             470             475             480
Gly Val Arg Cys Arg Ser Arg Ser Ile Gln Tyr Cys Val Pro Arg Asp
                485             490             495
Asp Ala Ala Pro Glu Ala Asp Gly Gln Ala Ala Gly Ala Leu Ala Ser
            500             505             510
Arg Asn Thr His Ser Ala Glu Leu Pro Pro Asp Gln Pro Ser Pro
        515             520             525
Cys Lys Cys Thr Cys Lys Lys Glu Pro Ser Ser Val Ser Pro Ser Ala
    530             535             540
Thr Val Lys Thr Arg Ser Thr Lys Ala Pro Pro His Leu Pro Leu
545             550             555             560
Ser Pro Ala Leu Thr Arg Ala Val Glu Gly Val Gln Tyr Ile Ala Asp
                565             570             575
His Leu Lys Ala Glu Asp Thr Asp Phe Ser Val Lys Glu Asp Trp Lys
            580             585             590
Tyr Val Ala Met Val Ile Asp Arg Ile Phe Leu Trp Met Phe Ile Ile
        595             600             605
Val Cys Leu Leu Gly Thr Val Gly Leu Phe Leu Pro Pro Trp Leu Ala
    610             615             620
Gly Met Ile
625

-continued

<210> SEQ ID NO 2
<211> LENGTH: 2149
<212> TYPE: DNA
<213> ORGANISM: Rattus norvegicus
<220> FEATURE:
<221> NAME/KEY: CDS
<222> LOCATION: (10)..(1902)
<223> OTHER INFORMATION: First CDS region
<300> PUBLICATION INFORMATION:
<308> DATABASE ACCESSION NUMBER: GenBank/NM_024354
<309> DATABASE ENTRY DATE: 2003-12-21

<400> SEQUENCE: 2

```
agcttcacc atg gcc aat tcg ggc ccc ggg gcg ccg ccg ctg ctg cta         51
          Met Ala Asn Ser Gly Pro Gly Ala Pro Pro Pro Leu Leu Leu
          1               5                  10 ctg ccg ctg ctg ctg ctc cta ggg acc ggc ctc ttg cct gct agc agc      99
Leu Pro Leu Leu Leu Leu Leu Gly Thr Gly Leu Leu Pro Ala Ser Ser
15              20                  25                  30 cac ata gag acc cgg gcc cat gcg gag gag cgg ctc ctg aag aga ctc     147
His Ile Glu Thr Arg Ala His Ala Glu Glu Arg Leu Leu Lys Arg Leu
            35                  40                  45 ttc tcc ggt tac aac aag tgg tct cgg cca gta ggc aat atc tca gat     195
Phe Ser Gly Tyr Asn Lys Trp Ser Arg Pro Val Gly Asn Ile Ser Asp
        50                  55                  60 gtg gtc ctc gtc cgc ttt ggc ttg tcc att gct cag ctc att gac gtg     243
Val Val Leu Val Arg Phe Gly Leu Ser Ile Ala Gln Leu Ile Asp Val
    65                  70                  75 gac gag aag aac cag atg atg aca acc aac gtg tgg gtg aag cag gag     291
Asp Glu Lys Asn Gln Met Met Thr Thr Asn Val Trp Val Lys Gln Glu
80                  85                  90 tgg cac gac tac aag ctg cgc tgg gac cct ggt gac tac gag aat gtc     339
Trp His Asp Tyr Lys Leu Arg Trp Asp Pro Gly Asp Tyr Glu Asn Val
95                  100                 105                 110 acc tcc atc cgc atc ccc tct gaa ctc atc tgg agg cct gac atc gtc     387
Thr Ser Ile Arg Ile Pro Ser Glu Leu Ile Trp Arg Pro Asp Ile Val
                115                 120                 125 ctc tac aac aat gcg gat gga gac ttt gca gtc acc cac ctg acc aag     435
Leu Tyr Asn Asn Ala Asp Gly Asp Phe Ala Val Thr His Leu Thr Lys
            130                 135                 140 gcc cac ctg ttc tat gac gga agg gtg cag tgg aca ccc cca gcc atc     483
Ala His Leu Phe Tyr Asp Gly Arg Val Gln Trp Thr Pro Pro Ala Ile
        145                 150                 155 tat aag agc tcc tgc agc atc gac gtc acc ttc ttc ccc ttt gac cag     531
Tyr Lys Ser Ser Cys Ser Ile Asp Val Thr Phe Phe Pro Phe Asp Gln
    160                 165                 170 cag aac tgt acc atg aag ttt gga tcc tgg acc tac gac aag gcc aag     579
Gln Asn Cys Thr Met Lys Phe Gly Ser Trp Thr Tyr Asp Lys Ala Lys
175                 180                 185                 190 att gac tta gtg agc att cat agc cgt gtg gac caa ctg gac ttc tgg     627
Ile Asp Leu Val Ser Ile His Ser Arg Val Asp Gln Leu Asp Phe Trp
                195                 200                 205 gaa agt ggg gag tgg gtc atc gtg gat gct gtg ggc acc tac aac acc     675
Glu Ser Gly Glu Trp Val Ile Val Asp Ala Val Gly Thr Tyr Asn Thr
            210                 215                 220 agg aag tac gag tgc tgt gcc gag atc tat cct gac atc acc tat gcc     723
Arg Lys Tyr Glu Cys Cys Ala Glu Ile Tyr Pro Asp Ile Thr Tyr Ala
        225                 230                 235 ttc atc atc cga cgc ctg ccg cta ttc tac acc atc aac ctc atc atc     771
Phe Ile Ile Arg Arg Leu Pro Leu Phe Tyr Thr Ile Asn Leu Ile Ile
    240                 245                 250
```

```
ccg tgc ctg ctc atc tcc tgt ctc acc gtg ctg gtc ttc tat ctg cct        819
Pro Cys Leu Leu Ile Ser Cys Leu Thr Val Leu Val Phe Tyr Leu Pro
255                 260                 265                 270 tca gag tgt ggc gag aag gtc aca ctg tgc atc tcg gtg ctg ctt tct        867
Ser Glu Cys Gly Glu Lys Val Thr Leu Cys Ile Ser Val Leu Leu Ser
            275                 280                 285 ctc acc gtc ttc ctg ctg ctc atc acc gag atc atc ccg tcc acc tcg        915
Leu Thr Val Phe Leu Leu Leu Ile Thr Glu Ile Ile Pro Ser Thr Ser
                290                 295                 300 ctg gtc atc ccg ctc atc ggc gag tac ctc ctc ttc acc atg atc ttc        963
Leu Val Ile Pro Leu Ile Gly Glu Tyr Leu Leu Phe Thr Met Ile Phe
                305                 310                 315 gtc acc ctc tcc atc gtc atc acg gtc ttc gtg ctc aat gtg cac cac       1011
Val Thr Leu Ser Ile Val Ile Thr Val Phe Val Leu Asn Val His His
            320                 325                 330 cgc tcg cca cgc aca cac acg atg ccc gcc tgg gtg cgt aga gtc ttc       1059
Arg Ser Pro Arg Thr His Thr Met Pro Ala Trp Val Arg Arg Val Phe
335                 340                 345                 350 ctg gac atc gtg cct cgc ctc ctc ttc atg aag cgc ccc tct gtg gtc       1107
Leu Asp Ile Val Pro Arg Leu Leu Phe Met Lys Arg Pro Ser Val Val
                355                 360                 365 aaa gac aac tgc cgg aga ctt att gag tcc atg cac aag atg gcc aac       1155
Lys Asp Asn Cys Arg Arg Leu Ile Glu Ser Met His Lys Met Ala Asn
            370                 375                 380 gcc ccc cgc ttc tgg cca gag cct gtg ggc gag ccc ggc atc ttg agt       1203
Ala Pro Arg Phe Trp Pro Glu Pro Val Gly Glu Pro Gly Ile Leu Ser
                385                 390                 395 gac atc tgc aac caa ggt ctg tca cct gcc cca act ttc tgc aac ccc       1251
Asp Ile Cys Asn Gln Gly Leu Ser Pro Ala Pro Thr Phe Cys Asn Pro
            400                 405                 410 acg gac aca gca gtc gag acc cag cct acg tgc agg tca ccc ccc ctt       1299
Thr Asp Thr Ala Val Glu Thr Gln Pro Thr Cys Arg Ser Pro Pro Leu
415                 420                 425                 430 gag gtc cct gac ttg aag aca tca gag gtt gag aag gcc agt ccc tgt       1347
Glu Val Pro Asp Leu Lys Thr Ser Glu Val Glu Lys Ala Ser Pro Cys
                435                 440                 445 cca tcg cct ggc tcc tgt cct cca ccc aag agc agc agt ggg gct cca       1395
Pro Ser Pro Gly Ser Cys Pro Pro Pro Lys Ser Ser Ser Gly Ala Pro
            450                 455                 460 atg ctc atc aaa gcc agg tcc ctg agt gtc cag cat gtg ccc agc tcc       1443
Met Leu Ile Lys Ala Arg Ser Leu Ser Val Gln His Val Pro Ser Ser
                465                 470                 475 caa gaa gca gca gaa gat ggc atc cgc tgc cgg tct cgg agt atc cag       1491
Gln Glu Ala Ala Glu Asp Gly Ile Arg Cys Arg Ser Arg Ser Ile Gln
480                 485                 490 tac tgt gtt tcc caa gat gga gct gcc tcc ctg gct gac agc aag ccc       1539
Tyr Cys Val Ser Gln Asp Gly Ala Ala Ser Leu Ala Asp Ser Lys Pro
495                 500                 505                 510 acc agc tcc ccg acc tcc ctg aag gcc gtt cca tcc cag ctt ccc gtg       1587
Thr Ser Ser Pro Thr Ser Leu Lys Ala Val Pro Ser Gln Leu Pro Val
                515                 520                 525 tca gac cag gcc tct cca tgc aaa tgc aca tgc aag gaa cca tct cct       1635
Ser Asp Gln Ala Ser Pro Cys Lys Cys Thr Cys Lys Glu Pro Ser Pro
            530                 535                 540 gtg tcc cca gtc act gtg ctc aag gcg gga ggc acc aaa gca cct ccc       1683
Val Ser Pro Val Thr Val Leu Lys Ala Gly Gly Thr Lys Ala Pro Pro
                545                 550                 555 caa cac ctg ccc ctg tca cca gcc ctg aca cgg gca gta gaa ggc gtc       1731
Gln His Leu Pro Leu Ser Pro Ala Leu Thr Arg Ala Val Glu Gly Val
560                 565                 570
```

| | | | | | | | | | | | | | | | |
|---|---|---|---|---|---|---|---|---|---|---|---|---|---|---|---|
| cag | tac | att | gca | gac | cac | ctc | aag | gca | gaa | gac | act | gac | ttc | tcg | gtg | 1779
| Gln | Tyr | Ile | Ala | Asp | His | Leu | Lys | Ala | Glu | Asp | Thr | Asp | Phe | Ser | Val |
| 575 | | | | 580 | | | | | 585 | | | | | 590 | | aag gag gac tgg aaa tac gtg gcc atg gtc att gac cga atc ttc ctc 1827
Lys Glu Asp Trp Lys Tyr Val Ala Met Val Ile Asp Arg Ile Phe Leu
            595             600             605 tgg atg ttc atc att gtc tgc ctt ctg ggc act gtg gga ctc ttc ctg 1875
Trp Met Phe Ile Ile Val Cys Leu Leu Gly Thr Val Gly Leu Phe Leu
            610             615             620 cct ccc tgg ctg gct ggt atg atc tag ggacgtggtg gtgcccagct 1922
Pro Pro Trp Leu Ala Gly Met Ile
            625             630 cccacatctc tgtagggcca tacgactcgt cagtcaccca catcttccaa accggctgac 1982 catgagacac cctaggagag agatgatgct tcttgggaga tggaagttgg ccctggttct 2042 agtcagacta tgggcgtggt tggagagaaa tgagggctga tacagttgca ggccgagtcc 2102 ccattaaagt ttctccagag caagtggcag tactccctga cttacag 2149

<210> SEQ ID NO 3
<211> LENGTH: 630
<212> TYPE: PRT
<213> ORGANISM: Rattus norvegicus

<400> SEQUENCE: 3

Met Ala Asn Ser Gly Pro Gly Ala Pro Pro Leu Leu Leu Leu Pro
1               5                   10                  15

Leu Leu Leu Leu Gly Thr Gly Leu Leu Pro Ala Ser Ser His Ile
            20                  25                  30

Glu Thr Arg Ala His Ala Glu Glu Arg Leu Leu Lys Arg Leu Phe Ser
            35                  40                  45

Gly Tyr Asn Lys Trp Ser Arg Pro Val Gly Asn Ile Ser Asp Val Val
        50                  55                  60

Leu Val Arg Phe Gly Leu Ser Ile Ala Gln Leu Ile Asp Val Asp Glu
65                  70                  75                  80

Lys Asn Gln Met Met Thr Thr Asn Val Trp Val Lys Gln Glu Trp His
                85                  90                  95

Asp Tyr Lys Leu Arg Trp Asp Pro Gly Asp Tyr Glu Asn Val Thr Ser
            100                 105                 110

Ile Arg Ile Pro Ser Glu Leu Ile Trp Arg Pro Asp Ile Val Leu Tyr
        115                 120                 125

Asn Asn Ala Asp Gly Asp Phe Ala Val Thr His Leu Thr Lys Ala His
    130                 135                 140

Leu Phe Tyr Asp Gly Arg Val Gln Trp Thr Pro Pro Ala Ile Tyr Lys
145                 150                 155                 160

Ser Ser Cys Ser Ile Asp Val Thr Phe Phe Pro Phe Asp Gln Gln Asn
                165                 170                 175

Cys Thr Met Lys Phe Gly Ser Trp Thr Tyr Asp Lys Ala Lys Ile Asp
            180                 185                 190

Leu Val Ser Ile His Ser Arg Val Asp Gln Leu Asp Phe Trp Glu Ser
        195                 200                 205

Gly Glu Trp Val Ile Val Asp Ala Val Gly Thr Tyr Asn Thr Arg Lys
    210                 215                 220

Tyr Glu Cys Cys Ala Glu Ile Tyr Pro Asp Ile Thr Tyr Ala Phe Ile
225                 230                 235                 240

Ile Arg Arg Leu Pro Leu Phe Tyr Thr Ile Asn Leu Ile Pro Cys
                245                 250                 255

```
Leu Leu Ile Ser Cys Leu Thr Val Leu Val Phe Tyr Leu Pro Ser Glu
            260                 265                 270

Cys Gly Glu Lys Val Thr Leu Cys Ile Ser Val Leu Leu Ser Leu Thr
        275                 280                 285

Val Phe Leu Leu Leu Ile Thr Glu Ile Ile Pro Ser Thr Ser Leu Val
290                 295                 300

Ile Pro Leu Ile Gly Glu Tyr Leu Leu Phe Thr Met Ile Phe Val Thr
305                 310                 315                 320

Leu Ser Ile Val Ile Thr Val Phe Val Leu Asn Val His His Arg Ser
                325                 330                 335

Pro Arg Thr His Thr Met Pro Ala Trp Val Arg Arg Val Phe Leu Asp
            340                 345                 350

Ile Val Pro Arg Leu Leu Phe Met Lys Arg Pro Ser Val Val Lys Asp
        355                 360                 365

Asn Cys Arg Arg Leu Ile Glu Ser Met His Lys Met Ala Asn Ala Pro
370                 375                 380

Arg Phe Trp Pro Glu Pro Val Gly Glu Pro Gly Ile Leu Ser Asp Ile
385                 390                 395                 400

Cys Asn Gln Gly Leu Ser Pro Ala Pro Thr Phe Cys Asn Pro Thr Asp
                405                 410                 415

Thr Ala Val Glu Thr Gln Pro Thr Cys Arg Ser Pro Pro Leu Glu Val
            420                 425                 430

Pro Asp Leu Lys Thr Ser Glu Val Glu Lys Ala Ser Pro Cys Pro Ser
        435                 440                 445

Pro Gly Ser Cys Pro Pro Lys Ser Ser Ser Gly Ala Pro Met Leu
450                 455                 460

Ile Lys Ala Arg Ser Leu Ser Val Gln His Val Pro Ser Ser Gln Glu
465                 470                 475                 480

Ala Ala Glu Asp Gly Ile Arg Cys Arg Ser Arg Ser Ile Gln Tyr Cys
                485                 490                 495

Val Ser Gln Asp Gly Ala Ala Ser Leu Ala Asp Ser Lys Pro Thr Ser
            500                 505                 510

Ser Pro Thr Ser Leu Lys Ala Arg Pro Ser Gln Leu Pro Val Ser Asp
        515                 520                 525

Gln Ala Ser Pro Cys Lys Cys Thr Cys Lys Glu Pro Ser Pro Val Ser
530                 535                 540

Pro Val Thr Val Leu Lys Ala Gly Gly Thr Lys Ala Pro Pro Gln His
545                 550                 555                 560

Leu Pro Leu Ser Pro Ala Leu Thr Arg Ala Val Glu Gly Val Gln Tyr
                565                 570                 575

Ile Ala Asp His Leu Lys Ala Glu Asp Thr Asp Phe Ser Val Lys Glu
            580                 585                 590

Asp Trp Lys Tyr Val Ala Met Val Ile Asp Arg Ile Phe Leu Trp Met
        595                 600                 605

Phe Ile Ile Val Cys Leu Leu Gly Thr Val Gly Leu Phe Leu Pro Pro
610                 615                 620

Trp Leu Ala Gly Met Ile
625                 630

<210> SEQ ID NO 4
<211> LENGTH: 4508
<212> TYPE: DNA
<213> ORGANISM: Mus musculus
<220> FEATURE:
<221> NAME/KEY: CDS
<222> LOCATION: (105)..(1994)
```

<223> OTHER INFORMATION: First CDS region
<300> PUBLICATION INFORMATION:
<308> DATABASE ACCESSION NUMBER: GenBank/NM_015730
<309> DATABASE ENTRY DATE: 2003-12-23

<400> SEQUENCE: 4

```
cgagcggccg cgacacgggg catgaagttg ggtgcgcgcg ggtctcggag cggaggcgcg        60
gtactgccgg gagccgccct cgtctagagc ccgttctgtg agcc atg gag atc ggc       116
                                                 Met Glu Ile Gly
                                                  1 ggc tcc ggg gcg ccg ccg ccg ctg ctc ctg ccg ctc ctg ctg ctc             164
Gly Ser Gly Ala Pro Pro Pro Leu Leu Leu Pro Leu Leu Leu Leu
  5              10                  15                  20 tta ggg acc ggc ctc ttg cct gct agc agc cac ata gag acc cgg gcc        212
Leu Gly Thr Gly Leu Leu Pro Ala Ser Ser His Ile Glu Thr Arg Ala
                 25                  30                  35 cat gcg gag gag cgg ctc ctg aag aga ctc ttc tct ggc tac aac aag        260
His Ala Glu Glu Arg Leu Leu Lys Arg Leu Phe Ser Gly Tyr Asn Lys
         40                  45                  50 tgg tct cgg cca gta gcc aat atc tca gat gtg gtc ctt gtc cgc ttt        308
Trp Ser Arg Pro Val Ala Asn Ile Ser Asp Val Val Leu Val Arg Phe
 55                  60                  65 ggc ttg tcg att gct cag ctc att gat gtg gat gag aaa aac cag atg        356
Gly Leu Ser Ile Ala Gln Leu Ile Asp Val Asp Glu Lys Asn Gln Met
 70                  75                  80 atg acg acc aac gtg tgg gtg aag cag gag tgg cat gac tac aaa ctg        404
Met Thr Thr Asn Val Trp Val Lys Gln Glu Trp His Asp Tyr Lys Leu
 85                  90                  95                 100 cgc tgg gac cct ggt gac tac gag aat gtc acc tcc atc cgc atc cca        452
Arg Trp Asp Pro Gly Asp Tyr Glu Asn Val Thr Ser Ile Arg Ile Pro
                105                 110                 115 tct gaa ctc atc tgg agg cct gac atc gtc ctc tac aac aac gcg gac        500
Ser Glu Leu Ile Trp Arg Pro Asp Ile Val Leu Tyr Asn Asn Ala Asp
                120                 125                 130 ggg gac ttt gca gtc acc cac cta acc aaa gcc cac ctg ttc tat gat        548
Gly Asp Phe Ala Val Thr His Leu Thr Lys Ala His Leu Phe Tyr Asp
                135                 140                 145 ggg cgt gtg cag tgg aca ccc ccg gcc atc tat aag agc tcc tgc agc        596
Gly Arg Val Gln Trp Thr Pro Pro Ala Ile Tyr Lys Ser Ser Cys Ser
        150                 155                 160 atc gac gtc acc ttc ttc ccc ttc gac cag cag aac tgt acc atg aag        644
Ile Asp Val Thr Phe Phe Pro Phe Asp Gln Gln Asn Cys Thr Met Lys
165                 170                 175                 180 ttt ggg tcc tgg acc tac gac aag gcc aag att gac ttg gtg agc atg        692
Phe Gly Ser Trp Thr Tyr Asp Lys Ala Lys Ile Asp Leu Val Ser Met
                185                 190                 195 cac agc cgt gtg gac caa ctg gac ttc tgg gaa agt ggg gag tgg gtc        740
His Ser Arg Val Asp Gln Leu Asp Phe Trp Glu Ser Gly Glu Trp Val
            200                 205                 210 att gtg gat gcc gtg ggc acc tac aac acc agg aag tat gaa tgc tgt        788
Ile Val Asp Ala Val Gly Thr Tyr Asn Thr Arg Lys Tyr Glu Cys Cys
            215                 220                 225 gcc gag atc tat cct gac atc acc tac gcc ttc atc atc cgc cga ctg        836
Ala Glu Ile Tyr Pro Asp Ile Thr Tyr Ala Phe Ile Ile Arg Arg Leu
    230                 235                 240 cca ctg ttc tac acc atc aac ctt atc atc ccg tgc ctg ctc atc tcc        884
Pro Leu Phe Tyr Thr Ile Asn Leu Ile Ile Pro Cys Leu Leu Ile Ser
245                 250                 255                 260 tgc ctc acc gtg ctg gtc ttc tat ctg ccc tcg gag tgc ggc gag aag        932
Cys Leu Thr Val Leu Val Phe Tyr Leu Pro Ser Glu Cys Gly Glu Lys
                265                 270                 275
```

-continued

| | | | | | | | | | | | | | | | | |
|---|---|---|---|---|---|---|---|---|---|---|---|---|---|---|---|---|
| gtc | acg | ctg | tgc | atc | tcg | gtg | ctg | ctt | tct | ctc | acc | gtc | ttc | ctg | ctg | 980 |
| Val | Thr | Leu | Cys | Ile | Ser | Val | Leu | Leu | Ser | Leu | Thr | Val | Phe | Leu | Leu | |
| | | 280 | | | | | 285 | | | | | 290 | | | | |
| ctc | atc | acc | gag | atc | atc | ccg | tcc | acc | tcg | ctg | gtc | atc | ccg | ctc | atc | 1028 |
| Leu | Ile | Thr | Glu | Ile | Ile | Pro | Ser | Thr | Ser | Leu | Val | Ile | Pro | Leu | Ile | |
| | | | 295 | | | | | 300 | | | | | 305 | | | |
| ggc | gag | tac | ctg | ctc | ttc | acc | atg | atc | ttc | gtc | acc | ctc | tcc | att | gtc | 1076 |
| Gly | Glu | Tyr | Leu | Leu | Phe | Thr | Met | Ile | Phe | Val | Thr | Leu | Ser | Ile | Val | |
| | 310 | | | | | 315 | | | | | 320 | | | | | |
| atc | acg | gtc | ttc | gtg | ctc | aat | gta | cac | cac | cgc | tca | cca | cgc | aca | cac | 1124 |
| Ile | Thr | Val | Phe | Val | Leu | Asn | Val | His | His | Arg | Ser | Pro | Arg | Thr | His | |
| 325 | | | | 330 | | | | | 335 | | | | | 340 | | |
| acc | atg | ccc | gcc | tgg | gtg | cgc | aga | gtc | ttc | ctg | gac | att | gtg | ccc | cgt | 1172 |
| Thr | Met | Pro | Ala | Trp | Val | Arg | Arg | Val | Phe | Leu | Asp | Ile | Val | Pro | Arg | |
| | | | | 345 | | | | | 350 | | | | | 355 | | |
| ctc | ctc | ttc | atg | aag | cgc | cca | tct | gtg | gtc | aaa | gac | aac | tgc | cgg | aga | 1220 |
| Leu | Leu | Phe | Met | Lys | Arg | Pro | Ser | Val | Val | Lys | Asp | Asn | Cys | Arg | Arg | |
| | | | 360 | | | | | 365 | | | | | 370 | | | |
| ctt | atc | gaa | tcc | atg | cac | aag | atg | gcc | aac | gcc | cct | cgt | ttc | tgg | cca | 1268 |
| Leu | Ile | Glu | Ser | Met | His | Lys | Met | Ala | Asn | Ala | Pro | Arg | Phe | Trp | Pro | |
| | 375 | | | | | 380 | | | | | 385 | | | | | |
| gag | cct | gag | agt | gag | ccc | ggc | atc | ttg | ggt | gac | atc | tgc | aac | caa | ggc | 1316 |
| Glu | Pro | Glu | Ser | Glu | Pro | Gly | Ile | Leu | Gly | Asp | Ile | Cys | Asn | Gln | Gly | |
| 390 | | | | | 395 | | | | | 400 | | | | | | |
| ctg | tca | cct | gcc | cca | act | ttc | tgc | aac | cgc | atg | gac | aca | gca | gtc | gag | 1364 |
| Leu | Ser | Pro | Ala | Pro | Thr | Phe | Cys | Asn | Arg | Met | Asp | Thr | Ala | Val | Glu | |
| 405 | | | | 410 | | | | | 415 | | | | | 420 | | |
| acc | cag | cct | aca | tgc | agg | tca | ccc | tcc | cac | aag | gtc | cct | gac | ttg | aag | 1412 |
| Thr | Gln | Pro | Thr | Cys | Arg | Ser | Pro | Ser | His | Lys | Val | Pro | Asp | Leu | Lys | |
| | | | | 425 | | | | | 430 | | | | | 435 | | |
| aca | tca | gag | gtt | gag | aag | gcc | agt | ccc | tgt | cca | tca | cct | ggc | tct | tgt | 1460 |
| Thr | Ser | Glu | Val | Glu | Lys | Ala | Ser | Pro | Cys | Pro | Ser | Pro | Gly | Ser | Cys | |
| | | | 440 | | | | | 445 | | | | | 450 | | | |
| cac | cca | ccc | aat | agc | agt | ggg | gcc | cca | gtg | ctc | atc | aaa | gcc | agg | tcc | 1508 |
| His | Pro | Pro | Asn | Ser | Ser | Gly | Ala | Pro | Val | Leu | Ile | Lys | Ala | Arg | Ser | |
| | | 455 | | | | | 460 | | | | | 465 | | | | |
| ctg | agc | gtc | cag | cat | gtg | ccc | agc | tcc | cag | gaa | gca | gcc | gag | ggc | agc | 1556 |
| Leu | Ser | Val | Gln | His | Val | Pro | Ser | Ser | Gln | Glu | Ala | Ala | Glu | Gly | Ser | |
| | 470 | | | | | 475 | | | | | 480 | | | | | |
| atc | cgc | tgc | cgg | tct | cgg | agt | atc | cag | tac | tgt | gtt | tcc | caa | gat | gga | 1604 |
| Ile | Arg | Cys | Arg | Ser | Arg | Ser | Ile | Gln | Tyr | Cys | Val | Ser | Gln | Asp | Gly | |
| 485 | | | | | 490 | | | | | 495 | | | | | 500 | |
| gct | gct | tcc | ctg | act | gag | agc | aag | ccc | act | ggc | tcc | cca | gcc | tcc | ctg | 1652 |
| Ala | Ala | Ser | Leu | Thr | Glu | Ser | Lys | Pro | Thr | Gly | Ser | Pro | Ala | Ser | Leu | |
| | | | | 505 | | | | | 510 | | | | | 515 | | |
| aag | acc | cgt | cca | tcc | cag | ctt | cca | gtg | tca | gac | cag | acc | tct | cca | tgc | 1700 |
| Lys | Thr | Arg | Pro | Ser | Gln | Leu | Pro | Val | Ser | Asp | Gln | Thr | Ser | Pro | Cys | |
| | | | 520 | | | | | 525 | | | | | 530 | | | |
| aaa | tgc | aca | tgc | aag | gaa | cca | tct | cct | gtg | tcc | ccc | atc | act | gtg | ctc | 1748 |
| Lys | Cys | Thr | Cys | Lys | Glu | Pro | Ser | Pro | Val | Ser | Pro | Ile | Thr | Val | Leu | |
| | | 535 | | | | | 540 | | | | | 545 | | | | |
| aag | gct | gga | ggc | acc | aaa | gca | cct | ccc | caa | cac | ctg | ccc | ctg | tca | cca | 1796 |
| Lys | Ala | Gly | Gly | Thr | Lys | Ala | Pro | Pro | Gln | His | Leu | Pro | Leu | Ser | Pro | |
| | 550 | | | | | 555 | | | | | 560 | | | | | |
| gcc | ctg | aca | cgg | gca | gta | gaa | ggc | gtc | cag | tac | att | gca | gac | cac | ctc | 1844 |
| Ala | Leu | Thr | Arg | Ala | Val | Glu | Gly | Val | Gln | Tyr | Ile | Ala | Asp | His | Leu | |
| 565 | | | | 570 | | | | | 575 | | | | | 580 | | |
| aag | gca | gaa | gac | aca | gac | ttc | tcg | gtg | aag | gag | gac | tgg | aaa | tac | gtg | 1892 |
| Lys | Ala | Glu | Asp | Thr | Asp | Phe | Ser | Val | Lys | Glu | Asp | Trp | Lys | Tyr | Val | |
| | | | | 585 | | | | | 590 | | | | | 595 | | |

```
gcc atg gtc att gac cga atc ttc ctc tgg atg ttc atc att gtc tgc      1940
Ala Met Val Ile Asp Arg Ile Phe Leu Trp Met Phe Ile Ile Val Cys
        600                 605                 610 ctt ctg ggc act gtg gga ctc ttc ctg cct cca tgg ttg gct ggt atg      1988
Leu Leu Gly Thr Val Gly Leu Phe Leu Pro Pro Trp Leu Ala Gly Met
            615                 620                 625 atc tag ggaatagcgg cacctagctc ccaggtctct acagggccat gcgactcgtc       2044
Ile agtcacccac atcttccaaa ccggccatga cacctagg agagagagat gctgccctgg      2104
ttgaccctgg ttctagtcag gccacaggcc tggttggagc tagttgagga ctgatatagt   2164
tacaggctga gtccctcatt aaagtttctc cagagcaagt gacagtcact ccctggctta   2224
cagacagcac acaccatct gtgtcacaga gaatgatcca gtgttgatct cagttgtcct    2284
ttgaggccaa acaattcat ccccccttcag gaaccagagc ccctcgtgct gtgggattcc   2344
tacggcccag gaaattccca tggtgctctg ctggccacac cctctccctc ccataatgt    2404 ggttccctca accctccagg ctgggctgct ctctgactca aaggtgtcag atgtaagccc   2464
cggcaggttt ttatttttgtt taggttgaag cgaattggta agaaatagag cagtgagata  2524
tgtggatgag tcccactcac aggtgaatga gtgcagggtc tcacaggaag agtgaggcac   2584
cacaggactc ctgcttccat ctcagggtca caggcatcaa tcatgagcat ttcctagggt   2644
ccataaaccc gaggagggca agggcataga gggtctcagg gttgtgatgg agccaaatcc   2704
tgtccagggc ctgggccgtt catcccctca tggatcttcc ttgatatccc tgtatgtttc   2764
tgcctctctg gaattagaag actgaaagta agatttctca tcacggtcct gtggtgtggc   2824
cacagttcac ctgagcacat ctctctagac cagtaggagt ggtgcgaagc cccttcaatg   2884
ttgtagaata gcgtgagctg ccaagagact tctaagcaaa acaggctctg tgactcattt   2944
ttcgagggcc atcgaccaag tcttagggggt gcctcaccct gtctgccttg cacttaggga  3004
agacccgaga ggttcctctt ccccttccca agatggcacc aggcaaccta gagaacccac   3064
cgtggtggga tgggagaacg aacatgctgt gcacatctct atgagattcc actgagtgaa   3124
gcccagaaca tgggaggcat gcaagaaatc accctgtgtc gtggtcccag ttgaccctcc   3184
gctgtctcca ccagccaggt gggtttcaca gagctgggcc ctgcaccctc agccaagctg   3244
ttctaggccc tgaagctgag gtccctgttt ggatagtcct ggggactgca gaatgaaaga   3304
agaacttaat gaacgcacca agcctccagt aggtacggct gccacctccg tggtatgact   3364
tgcccatccc agctgaatga ggatgtcagg aaggaggtat gccagagggc cagcattgcc   3424
tttacctgac tacctacagg caaatccacc tttaaacaca gagctgctgg acatccaggg   3484
tgctggtggg aaaggaactc cacactggga gccccaggcc attcctatga acaggaaggg   3544
gatgcagagg cctggtctct gaactctgga tattgttcca ggtcttccct agagtcctaa   3604
gggcatcgag gatcccatct gccatgtttc agtctgccct ccactgactg actagatctc   3664
tagcccctat attggaactg tcgggatgct gcaagatgac cctggtgggg aaattcatgc   3724
cagaatctgg gaccaagggg aacacaagcc ccagtgatga agacagcagg taacacctga   3784
cagatgtgtg ttctaccatt atggtgcata cgtggctcca accacaagaa atgcagacaa   3844
cagtggagat cagggcaagg ccattgtgac atggaacagg accgctgtgc tggtctcttc   3904
agggttagga aaactgaact gctgggatgc tcctgacagg ctacccactt cccctaccc    3964 cccaacacac attcacaagc cagaaaagga aaataaaaca ccgtgttctc cccattccca   4024
ctcagccggc cttttgtctg cctgcttcca gtgttgatat gtgttcaaga taaagttcag   4084
```

-continued

```
ttagggcaga atgcttgatt taagactttt gaaccagtga gctttaaaga acagagactg    4144
tgtggcccca gcccctctga tacgtagaca ttatctcccc aaagctccca gtcctcccag    4204
tctaccccat cccattagac agcatcaact caaatgtgag tcttggagac cagttcggct    4264
agccatcata tgtctgggaa tcccatattg gactctgcaa tgtctggctt ctttcgcttg    4324
tgtggccaag gctcatctgc ggtgttgtgt gtgatagact cattgctgtt gtgtgcttgt    4384
tggatcttag ttgtttctgt ctgaataaac cgagtcgtgg tgtcttcccc caaaaaaaaa    4444 aaaaaaaaa aaaaaaaaaa aaaaaaaaaa aaaaaaaaa aaaaaaaaaa aaaaaaaaaa    4504
aaaa                                                                  4508
```

<210> SEQ ID NO 5
<211> LENGTH: 629
<212> TYPE: PRT
<213> ORGANISM: Mus musculus

<400> SEQUENCE: 5

```
Met Glu Ile Gly Gly Ser Gly Ala Pro Pro Leu Leu Leu Pro
1               5                   10                  15

Leu Leu Leu Leu Leu Gly Thr Gly Leu Leu Pro Ala Ser Ser His Ile
            20                  25                  30

Glu Thr Arg Ala His Ala Glu Glu Arg Leu Leu Lys Arg Leu Phe Ser
        35                  40                  45

Gly Tyr Asn Lys Trp Ser Arg Pro Val Ala Asn Ile Ser Asp Val Val
    50                  55                  60

Leu Val Arg Phe Gly Leu Ser Ile Ala Gln Leu Ile Asp Val Asp Glu
65                  70                  75                  80

Lys Asn Gln Met Met Thr Thr Asn Val Trp Val Lys Gln Glu Trp His
                85                  90                  95

Asp Tyr Lys Leu Arg Trp Asp Pro Gly Asp Tyr Glu Asn Val Thr Ser
            100                 105                 110

Ile Arg Ile Pro Ser Glu Leu Ile Trp Arg Pro Asp Ile Val Leu Tyr
        115                 120                 125

Asn Asn Ala Asp Gly Asp Phe Ala Val Thr His Leu Thr Lys Ala His
    130                 135                 140

Leu Phe Tyr Asp Gly Arg Val Gln Trp Thr Pro Pro Ala Ile Tyr Lys
145                 150                 155                 160

Ser Ser Cys Ser Ile Asp Val Thr Phe Phe Pro Phe Asp Gln Gln Asn
                165                 170                 175

Cys Thr Met Lys Phe Gly Ser Trp Thr Tyr Asp Lys Ala Lys Ile Asp
            180                 185                 190

Leu Val Ser Met His Ser Arg Val Asp Gln Leu Asp Phe Trp Glu Ser
        195                 200                 205

Gly Glu Trp Val Ile Val Asp Ala Val Gly Thr Tyr Asn Thr Arg Lys
    210                 215                 220

Tyr Glu Cys Cys Ala Glu Ile Tyr Pro Asp Ile Thr Tyr Ala Phe Ile
225                 230                 235                 240

Ile Arg Arg Leu Pro Leu Phe Tyr Thr Ile Asn Leu Ile Ile Pro Cys
                245                 250                 255

Leu Leu Ile Ser Cys Leu Thr Val Leu Val Phe Tyr Leu Pro Ser Glu
            260                 265                 270

Cys Gly Glu Lys Val Thr Leu Cys Ile Ser Val Leu Leu Ser Leu Thr
        275                 280                 285

Val Phe Leu Leu Leu Ile Thr Glu Ile Ile Pro Ser Thr Ser Leu Val
    290                 295                 300
```

-continued

```
Ile Pro Leu Ile Gly Glu Tyr Leu Leu Phe Thr Met Ile Phe Val Thr
305                 310                 315                 320

Leu Ser Ile Val Ile Thr Val Phe Val Leu Asn Val His His Arg Ser
                325                 330                 335

Pro Arg Thr His Thr Met Pro Ala Trp Val Arg Val Phe Leu Asp
            340                 345                 350

Ile Val Pro Arg Leu Leu Phe Met Lys Arg Pro Ser Val Lys Asp
        355                 360                 365

Asn Cys Arg Arg Leu Ile Glu Ser Met His Lys Met Ala Asn Ala Pro
    370                 375                 380

Arg Phe Trp Pro Glu Pro Glu Ser Glu Pro Gly Ile Leu Gly Asp Ile
385                 390                 395                 400

Cys Asn Gln Gly Leu Ser Pro Ala Pro Thr Phe Cys Asn Arg Met Asp
                405                 410                 415

Thr Ala Val Glu Thr Gln Pro Thr Cys Arg Ser Pro Ser His Lys Val
            420                 425                 430

Pro Asp Leu Lys Thr Ser Glu Val Glu Lys Ala Ser Pro Cys Pro Ser
        435                 440                 445

Pro Gly Ser Cys His Pro Pro Asn Ser Ser Gly Ala Pro Val Leu Ile
450                 455                 460

Lys Ala Arg Ser Leu Ser Val Gln His Val Pro Ser Ser Gln Glu Ala
465                 470                 475                 480

Ala Glu Gly Ser Ile Arg Cys Arg Ser Arg Ser Ile Gln Tyr Cys Val
                485                 490                 495

Ser Gln Asp Gly Ala Ala Ser Leu Thr Glu Ser Lys Pro Thr Gly Ser
            500                 505                 510

Pro Ala Ser Leu Lys Thr Arg Pro Ser Gln Leu Pro Val Ser Asp Gln
        515                 520                 525

Thr Ser Pro Cys Lys Cys Thr Cys Lys Glu Pro Ser Pro Val Ser Pro
    530                 535                 540

Ile Thr Val Leu Lys Ala Gly Gly Thr Lys Ala Pro Pro Gln His Leu
545                 550                 555                 560

Pro Leu Ser Pro Ala Leu Thr Arg Ala Val Glu Gly Val Gln Tyr Ile
                565                 570                 575

Ala Asp His Leu Lys Ala Glu Asp Thr Asp Phe Ser Val Lys Glu Asp
            580                 585                 590

Trp Lys Tyr Val Ala Met Val Ile Asp Arg Ile Phe Leu Trp Met Phe
        595                 600                 605

Ile Ile Val Cys Leu Leu Gly Thr Val Gly Leu Phe Leu Pro Pro Trp
610                 615                 620

Leu Ala Gly Met Ile
625
```

US 8,173,859 B2

EPILEPSY MODEL ANIMAL

This application is a U.S. national stage of International Application No. PCT/JP2005/003430 filed Feb. 23, 2005.

TECHNICAL FIELD

The invention of this patent application relates to an epilepsy model animal having gene abnormality homologous to human autosomal dominant nocturnal frontal lobe epilepsy and developing spontaneous epileptic seizure during sleep.

BACKGROUND ART

Epilepsy is a chronic brain disorder characterized by episodic seizures caused by excessive brain cell firing. The excessive brain cell firing is a result of various etiologic factors, and, accordingly, progression and prognosis of the seizure can vary greatly depending on the type of epilepsy. Therefore, accurate diagnosis and appropriate procedure are required for treating epilepsy.

An epilepsy model animal has been used as means for developing and progressing diagnostic and treatment methods of epilepsy. As the epilepsy model animal, drug-induced epileptic animals produced by administration of kainic acid and kindling (method of repeating brain stimulation with electricity under a threshold value)-induced epileptic animals have heretofore been used.

However, the conventional model animals are not more than animals in which convulsive seizure is forcibly induced and could not be used as true models for human epilepsy although they could be used as model animals of "convulsive seizure".

Meanwhile, thanks to recent progress in molecular biological studies, gene abnormality is being identified in several types of epilepsy. The inventors of this invention have found that there is a relationship between human chromosomal dominant nocturnal frontal lobe epilepsy and mutation of a neuron nicotinic acetylcholine receptor α4 subunit (CHRNA4) gene (Non-Patent Document 1) and that the mutation of CHRNA4 is specifically a substitution of Ser at position 284 by Leu (Non-Patent Document 2).

Non-Patent Document 1: Hirose, S. et al., Neurology 53: 1749-1753, 1999.
Non-Patent Document 2: Matsushima, N. et al., Epilepsy Res. 48: 181-186, 2002.

DISCLOSURE OF THE INVENTION

The invention of this patent application has been accomplished in view of the problems of the conventional epilepsy model animals described above, and an object thereof is to provide a novel epilepsy model animal having gene abnormality (expression of mutant CHRNA4) homologous to human autosomal dominant nocturnal frontal lobe epilepsy and spontaneously presenting a somatic symptom identical to that of human autosomal dominant nocturnal frontal lobe epilepsy (epileptic seizure during sleep).

This patent application provides, as an invention for solving the above-described problems, an epilepsy model animal (CHRNA4:S284L) developing spontaneous epileptic seizure during sleep, which is a nonhuman animal established by ontogenesis of a totipotent cell into which a polynucleotide encoding nonhuman mutant CHRNA4 is introduced and having said polynucleotide in its somatic chromosome, or a progeny of the nonhuman animal, wherein said nonhuman mutant CHRNA4 has the corresponding mutation of human mutant CHRNA4 in which the 284th Ser of SEQ ID NO: 1 is substituted by Leu.

In a preferred mode of the epilepsy model animal (CHRNA4:S284L), the polynucleotide encoding the nonhuman mutant CHRNA4 is fused with a polynucleotide corresponding to a promoter region of a gene specifically expressing in cerebrum cortex and hippocampus.

Further, in another preferred mode of the epilepsy model animal (CHRNA4:S284L) of this invention, the nonhuman animal is a rat, and the polynucleotide encodes rat mutant CHRNA4 having the nucleotide sequence of SEQ ID NO: 2 in which the 865th c is substituted by t, and the 866th t is substituted by c.

In this invention, "polynucleotide" means a molecule obtainable by binding plural phosphoric esters (nucleotide ATP, GTP, CTP, and UTP or dATP, dGTP, dCTP, and dTTP) of a nucleotide in which purine or pyrimidine is β-N-glycoside-bound to sugar.

Also, "nonhuman mutant CHRNA4 corresponding to human mutant CHRNA4" means that Ser of a nonhuman CHRNA4 corresponding to Ser at position 284 of a human CHRNA4 (SEQ ID NO: 2) is substituted by Leu.

Other terms and concepts in this invention will be defined in detail in "Best Mode for Carrying out the Invention" and "Examples". Further, various technologies used for carrying out this invention other than those whose sources are indicated can be practiced by person skilled in the art easily and without fail based on known publications and the like. For example, the technologies of gene engineerings and molecular biology are described in Sambrook and Maniatis, in Molecular Cloning—A Laboratory Manual, Cold Spring Harbor Laboratory Press, New York, 1989; Ausubel, F. M et al., Current Protocols in Molecular Biology, John Wiley & Sons, New York, N.Y., 1995, and the like.

BEST MODE FOR CARRYING OUT THE INVENTION

It is possible to create the epilepsy model animal of this invention (CHRNA4:S284L) from various types of nonhuman mammals. For example, it is possible to create the epilepsy model animal from a mouse, a rat, a rabbit, a cat, a dog, a pig, a horse, a cow, and the like, and it is preferable to use the mouse or the rat in view of versatility and convenience as a laboratory animal.

As the "polynucleotide encoding the nonhuman mutant CHRNA4" to be introduced, a mutant CHRNA4 polynucleotide corresponding to the subject animal species is used. For example, an amino acid sequence (SEQ ID NO: 5) of a mouse CHRNA4 and a sequence (SEQ ID NO-4) of a polynucleotide (cDNA) encoding the amino acid sequence are known (GenBank/NM-015730), and Ser at position 286 of SEQ ID NO: 5 is corresponding to Ser at position 284 of the human CHRNA4. Therefore, it is possible to create a "polynucleotide encoding a mouse mutant CHRNA4" by substituting a Ser codon (tct) at positions 960 to 962 of SEQ ID NO: 4 by a Leu codon (ctt, ctc, cta, ctg, tta, or ttg). Also, an amino acid sequence (SEQ ID NO: 3) of a rat CHRNA4 and a sequence (SEQ ID NO: 2) of a polynucleotide (cDNA) encoding the amino acid sequence are known (GenBank/NM-024354), and Ser at position 286 of SEQ ID NO: 3 is corresponding to Ser at position 284 of the human CHRNA4. Therefore, it is possible to create a "polynucleotide encoding a rat mutant CHRNA4" by substituting a Ser codon (tct) at positions 865 to 867 of SEQ ID NO: 2 by a Leu codon (ctt, ctc, cta, ctg, tta, or ttg). It is possible to perform the nucleotide substitution by a method using a commercially available mutant introduction kit or a known method such as the mutant introduction PCR.

It is also preferable to introduce the polynucleotide encoding the nonhuman mutant CHRNA4 as a fusion polynucleotide of the polynucleotide and a polynucleotide corresponding to a promoter region of a gene specifically expressing in brain cortex and hippocampus. As the promoter region, it is possible to use a PDGF-β chain promoter and the like.

It is possible to create the epilepsy model animal (CHRNA4:S284L) of this invention in accordance with a known transgenic animal creation method (for example, Proc. Natl. Acad. Sci. USA 77; 7380-7384, 1980). That is, it is possible to create a target transgenic animal by: introducing the polynucleotide (preferably the fused polynucleotide) into differentiating totipotent cells of the nonhuman animal; generating individuals from the cells; and selecting one into whose somatic genome the introduced polynucleotide is implanted from the individuals.

It is possible to use a fertilized egg or an early embryo as the differentiating totipotent cell into which the polynucleotide is introduced. As a method for gene introduction into a cultured cell, DNA physical injection (microinjection) is optimum in view of a high yield of transgenic animal individuals and efficiency of transmitting the introduced gene to the next generation. The fertilized eggs into which the gene is injected are transplanted to fallopian tube of a foster parent to develop individuals, and borne animals are raised by a foster parent. Then, a DNA is extracted from a part (tip of tail or the like) of the body of each of the animals to confirm existence of the introduced polynucleotide by Southern analysis or PCR. The individual (heterozygote) in which the existence of the introduced polynucleotide is confirmed is a founder (Founder: F0), and the introduced gene is transmitted to 50% of its descendants (F1). Further, it is possible to create individuals (F2) having the introduced gene in both of diploid chromosomes by crossing a male and a female of the F1 individuals.

As the method for introducing an exogenous gene, to a chromosomal DNA of an animal individual, the knock in method using a known target gene recombinant method (Gene Targeting Method: Science 244: 1288-1292, 1989) is known. In the knock in method, an endogenous gene existing in a chromosomal DNA of an animal individual is perfectly substituted by an exogenous gene. Therefore, the gene introduced-animal created by the knock in method does not produce the endogenous proteins but produces only exogenous (mutant) proteins homologous to the endogenous proteins. In contrast, the transgenic method used for the creation of the epilepsy model animal of this invention is capable of newly introducing the polynucleotide encoding the mutant CHRNA4 at an arbitrary position of a chromosomal DNA of an endogenous gene while maintaining the endogenous gene (CHRNA4 gene) in a normal state. Therefore, both of the normal CHRNA4 and the mutant CHRNA4 are produced in the epilepsy model animal of this invention. A neuron nicotinic acetylcholine receptor is a protein functioning as an ion channel (2 α subunits and 3 β subunits), and a channel function of such ion channel is modified when any one of the subunits is mutated. Therefore, the normal subunit and the mutant subunit may be expressed simultaneously, and the inventors of this invention have accomplished this invention based on the concept of considering the simultaneous expression of the normal subunit and the mutant subunit is more appropriate for a model animal presenting human epileptic seizure than the expression of the mutant subunit achieved by the knock in method.

The epilepsy model animal of this invention (CHRNA4: S284L) has the excellent characteristic of having spontaneous epileptic seizure during sleep as described in Examples, which is the same as that of human chromosomal dominant nocturnal epilepsy.

EXAMPLES

Hereinafter, the invention of this patent application will be described in more detail and specifically by way of examples, but the invention of this patent application is not limited by the following examples.

(1) Method (1-1) Creation of Transgenic Rats

PCR amplification of a rat fetus cDNA panel (Clontech, Palo Alto, Calif.) was performed for obtaining cDNAs of a rat Chrna4 and a rat Chrnb2, and then the cDNAs were subjected to sub cloning in a pCRTOPO II vector (Invitrogen, Carlsbad, Calif.). A nucleotide substitution (substitution of C at position 865 of SEQ ID NO: 2 by T, substitution of T at position 866 of SEQ ID NO: 2 by C; S286L) causing missense displacement corresponding to human nocturnal frontal lobe epilepsy was introduced in the Chrna4 cDNA by using Quickchange Site-Directed Mutagenesis Kit (Stratagene, La Jolla, Calif.). Into pSP64 Poly(A) vector (Promega, Madison, Wis.), cDNAs of a Wildtype Chrana4, a Chrnb2, and a mutant Chrna4 were introduced to create corresponding cRNAs, and the cRNAs were used for in vitro electrical biological study using xenopus oocytes. The mutant Chrna4 cDNA was inserted into an expression vector retaining a human PDGF-P chain promoter of pCI-neo vector (Promega). Integrity of each of the clones was confirmed by plural times of sequencing using a series of sequencing primers for each of the cloning steps. The vector retaining the mutant Chrna4 cDNA was cleaved by using Sna KI and NAe I, followed by purification of a chain fragment containing the mutant cDNA and the PDGF-β promoter. The fragment was injected into rat oocytes (SD) in Japan SLC, Inc. (Hamamatsu) to create transgenic rats.

(1-2) Confirmation of Genotypes of Transgenic Rats

Tissue obtained by cutting a tale of each of the transgenic rats was digested overnight in a buffer solution [50 mM of Tris (pH 8), 10 mM of EDTA, 100 mM of sodium chloride, 1% (w/v) of SDS, and 50 mg/ml of proteinase K (Sigma)] at 55° C. After an Rnase A treatment (100 μg/ml, at 37° C. for 1 hour), ammonium acetate was added until a final concentration reached 2 M, followed by cooling, and then centrifugation was performed to precipitate a protein. A DNA in a supernatant was precipitated by using 0.6 vol of cool isopropanol, followed by washing with 70% ethanol. DNA pellets were dissolved into water at 4° C. overnight. An amount of the DNA was evaluated at an optical density of 260 nm, and a part (50 ng) of the DNA was subjected to PCR amplification. The PCR product was subjected to sequencing with the use of an automatic sequence deciding apparatus (ABI 3100: Perkin Elmer Biosystems, Foster City, Calif.).

As a result, it was confirmed that each of the created transgenic rats had the introduced mutant Chrna4 cDNA in its somatic chromosome.

(1-3) Measurement of Brain Waves (EEG) of Transgenic Rats

Electroencephalography of each of the 8 to 10 weak-old transgenic rats was performed. After anesthesia using halothane (1.5% mixture of halothane and $O_2$ and $N_2O$), the rat was fixed to a brain fixing device, and then a Teflon (trademark) coating stainless electrode for electroencephalography was attached to the frontal lobe of each of right and left cerebral hemispheres (A=3.2 mm, L=0.8 mm from bregma), followed by fixing with dental cement. An indifferent electrode was embedded in an upper part of the cerebellum. Brain wave was measured by using a telemeter (Unimec Co., Tokyo, Japan) set to 0.1±3 kHz under the free motion condition from after 7 days from the attachment of electrodes. Brain wave analysis was performed also by using Chart for windows (Adinsruments, Sydney, Australia).

Figure 1:
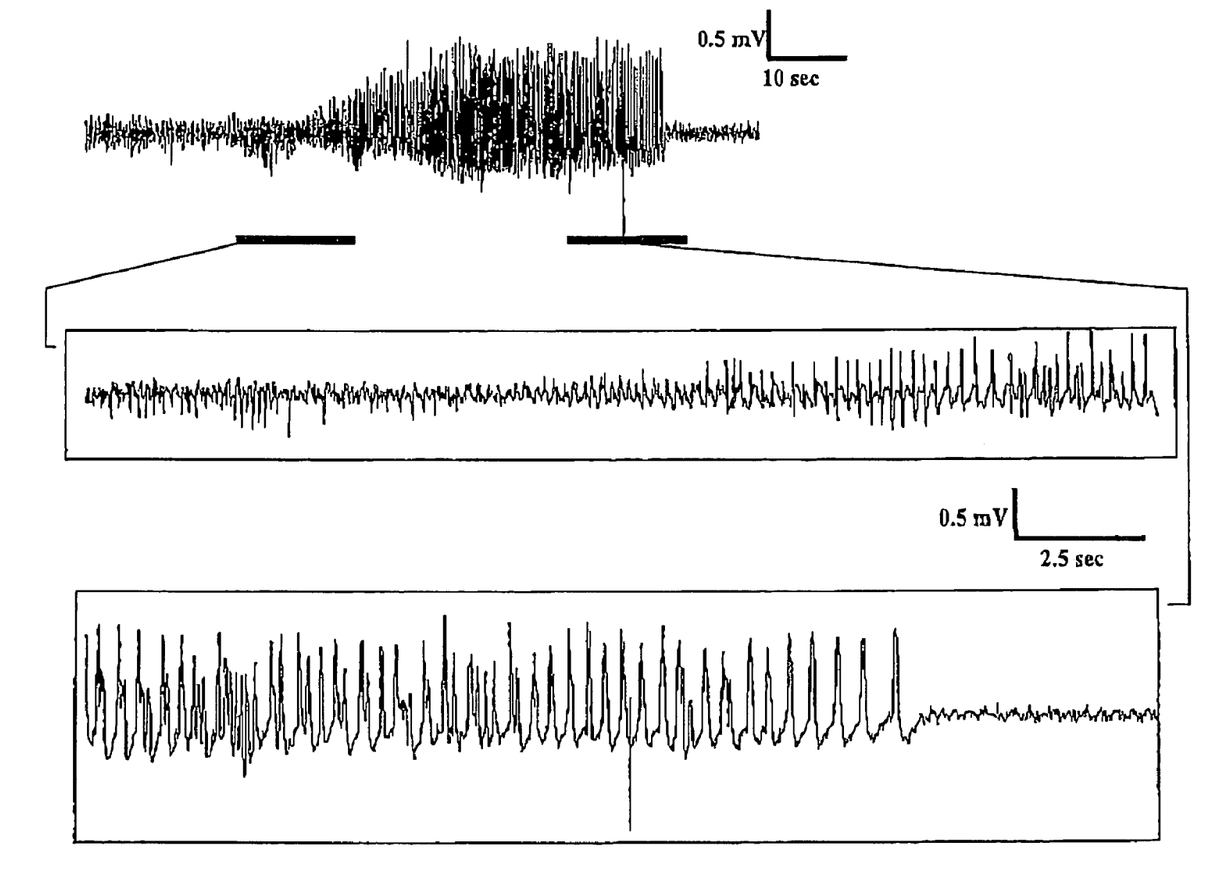
FIG. 1 is a diagram showing electroencephalogram recording during sleep of the epilepsy model animal of this invention. Shown in an upper part is the recording for 60 minutes; shown in a middle part is the recording of a cluster of spikes (for 15 seconds); and shown in a lower part is the recording of transition from the cluster of spikes to a slow wave complex, a gradual reduction in frequency, and a gradual increase in amplification (for 15 seconds).

Results are as shown in FIG. 1. After a spindle wave characteristic of a nap, a cluster of spikes (middle part in FIG. 1) characteristic of the epileptic seizure was maintained for over ten seconds, followed by transition to a slow wave complex, a gradual reduction in frequency, and a gradual increase in amplification (lower part in FIG. 1), whereby the epileptic seizure transitioned from the partial seizure to secondary general seizure.

As described in the foregoing, the created transgenic rat expressed mutant CHRNA4 and had the epileptic seizure during sleep. From the genotype of expressing the mutant CHRNA4 and the somatic symptom of epileptic seizure during sleep, it was confirmed that the transgenic rat was suitable as a model animal for human chromosomal dominant nocturnal frontal lobe epilepsy.

Industrial Applicability

As described in detail in the foregoing, the invention of this patent application provides an animal having gene abnormality homologous to human chromosomal dominant nocturnal frontal lobe epilepsy and having a somatic symptom identical to that of the human chromosomal dominant nocturnal frontal lobe epilepsy (epileptic seizure during sleep). This epilepsy model animal is remarkably useful for developments of diagnostic method and therapy for the human chromosomal dominant nocturnal frontal lobe epilepsy.

The invention claimed is:

1. A transgenic rat whose genome comprises both a normal CHRNA4 gene and a transgene encoding mutant CHRNA4, wherein the transgene encodes the amino acid sequence of SEQ ID NO:3 in which the 286th Ser is substituted by Leu and is operably linked to a PDGF-β chain promoter and expressed in the brain cortex and hippocampus of the transgenic rat, and wherein the transgenic rat is established by a normal ontogenesis and develops a spontaneous epileptic seizure during sleep.

2. The transgenic rat of claim 1, wherein the mutant transgene CHRNA4 has the nucleotide sequence of SEQ ID NO:2 in which the 865th t is substituted by c, and the 866th c is substituted by t.

* * * * *